United States Patent
Hansenne et al.

(12)

(10) Patent No.: US 6,432,389 B1
(45) Date of Patent: Aug. 13, 2002

(54) HIGH SPF NONTACKY/NONGREASY UV-PHOTOPROTECTING COMPOSITIONS COMPRISING PARTICULATES OF MMA CROSSPOLYMERS

(75) Inventors: Isabelle Hansenne, Westfield; Donald W. Rick, Dumont, both of NJ (US)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/899,296

(22) Filed: Jul. 6, 2001

(51) Int. Cl.[7] .............................. A61K 7/42; A61K 7/44; A61K 7/00; A61K 31/74
(52) U.S. Cl. ........................ 424/59; 404/60; 404/78.02; 404/78.08; 404/400; 404/401
(58) Field of Search .............................. 424/89, 78.02, 424/78.08, 60, 400, 401

(56) References Cited

U.S. PATENT DOCUMENTS 5,166,355 A  * 11/1992 Leistner et al. ............. 548/260
5,237,071 A  *  8/1993 Leistner et al. ............. 548/260

* cited by examiner

*Primary Examiner*—Shelley A. Dodson
(74) *Attorney, Agent, or Firm*—Burns, Doane, Swecker & Mathis, L.L.P.

(57) ABSTRACT

Topically applicable cosmetic/dermatological compositions well suited for the UV-photoprotection of human skin, hair and/or scalp, contain (a) an effective UV-photoprotecting amount of at least one UV-A and/or UV-B sunscreen and (b) an amount of a methyl methacrylate crosspolymer effective to, on application of the composition, reduce the greasiness/diffusion and improve the dryness thereof, formulated into (c) a topically applicable, cosmetically/dermatologically acceptable vehicle, diluent or carrier therefor.

20 Claims, No Drawings

HIGH SPF NONTACKY/NONGREASY UV-PHOTOPROTECTING COMPOSITIONS COMPRISING PARTICULATES OF MMA CROSSPOLYMERS

BACKGROUND OF THE INVENTION

1. Technical Field of the Invention

The present invention relates to novel cosmetic/dermatological compositions for topical application, for the ultraviolet (UV)-photoprotection of the skin and/or the hair against the damaging effects of UV radiation, in particular solar radiation, and to the use of same for the aforesaid cosmetic/dermatological indications.

This invention more especially relates to topically applicable, high SPF UV-A and/or UV-B sunscreen compositions comprising particulates of a methyl methacrylate ("MMA") crosspolymer, such compositions being well suited as "sport" products, namely, the subject formulations do not diffuse into the eyes and are dry, pleasant, less shiny and waterproof on application, as well as nontacky, nongreasy and nonwaxy to the touch.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the case of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin is known to this art.

These photoprotective/sunscreen compositions are quite often oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

Also, there exists an increasing demand for higher SPF suncare products. High SPFs can be attained by incorporating more sunscreens at elevated levels; however, this is not always feasible, as sunscreens add considerable cost to the formulation and high sunscreen levels can promote increased irritancy.

Corollary thereto, the dibenzoylmethane sunscreen avobenzone, for example, is a particularly attractive chemical UV-absorber/filter. But it is even more difficult to formulate high SPF sunscreen products when the formulation contains avobenzone.

Much more difficult is the formulation of high SPF avobenzone sprayable compositions. Indeed, high SPF sunscreen sprays are commercially available, but these do not contain avobenzone. Typically, high SPF values are obtained by formulating high levels of UV-B absorbing sunscreens, such as octylmethoxy cinnamate. Nonetheless, these formulations provide no protection against longer wavelength UV-A irradiation.

Too, sunscreen compositions are also know to this art that are marketed specifically as "sport" products. These must provide or deliver, for example, the following benefits: high SPF, waterproof, the product must not diffuse into the eyes, and the product must be dry on application without leaving a greasy residue on the hands.

Compare, for example, Schering-Plough's U.S. Pat. No. 5,914,102, relating to high SPF perspiration-resistant sport sunscreen compositions, an oil phase of which comprising submicron silica particles having a hydrophobic surface.

Nonetheless, the prior art high SPF sunscreen compositions suited for "sport" applications remain at least somewhat lacking in terms of total consumer acceptance, in that they continue to provide, on application, an at least somewhat objectionable tacky, greasy and/or waxy feel.

SUMMARY OF THE INVENTION

It has now unexpectedly and surprisingly been determined that formulating particulates of methyl methacrylate crosspolymers into UV-photoprotecting sunscreen compositions significantly reduces diffusion of the product and also reduces the tacky/greasy/waxy feel thereof, making it dry and pleasant on application to human skin, hair and/or scalp.

DETAILED DESCRIPTION OF BEST MODE AND SPECIFIC/PREFERRED EMBODIMENTS OF THE INVENTION

More particularly according to the present invention, methyl methacrylate crosspolymer is a synthetic copolymer of methyl methacrylate crosslinked with glycol dimethacrylate. It has the empirical formula:

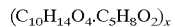

and has been assigned Chemical Abstracts Service (CAS) No. 25777-71-3. It is also described at page 808, volume 1, *International Cosmetic Ingredient Dictionary and Handbook* (Seventh Edition, 1997), published by The Cosmetic, Toiletry, and Fragrance Association (Washington, D.C.).

One methyl methacrylate crosspolymer according to the invention is commercially available from Presperse Incorporated, Piscataway, N.J., under the trademark Ganzpearl GMP-0820. The product specifications of Ganzpearl GMP-0820 include: spherical, white fine powder having a particle size of 4–10.5 $\mu$m, preferably 4–8 $\mu$m, high oil absorption, creamy feel, good slip, specific gravity of 1.10 to 1.25, film-forming, viscosity increasing. Its loss on ignition (400° C.) is less than 0.1%, and on drying (105° C./2 hours) is less than 2.0%. The surface residual monomer content of Ganzpearl GMP-0820 is less than 20 ppm, with total residual monomer content being less than 100 ppm. Too, the crosslinking density of this very high molecular weight polymer is on the order of 43 wt % [crosslinking monomer/(crosslinking monomer+base monomer)].

Methyl methacrylate crosspolymers are also commercially available from Nihon Junyaku under the trademark Jurymer MB-1P and from Tomer under the trademark Microsphere M-305.

Characteristically, the particulates of methyl methacrylate crosspolymers according to this invention have a particle size of less than 20 μm, preferably less than 10 μm.

Consistent herewith, dry, nongreasy, nontacky and non-waxy sunscreen formulations are provided by the addition of methyl methacrylate crosspolymer into a wide variety of sunscreen compositions, and formulated into conventional topically applicable, cosmetically/dermatologically acceptable vehicles, diluents or carriers therefor.

It too should be appreciated that formulating a sunscreen product with good aesthetics that is dry and nongreasy on application is particularly difficult if the photostabilized compositions contain on the order of 10% octocrylene, which is a viscous and sticky oil.

While not wishing to be bound to or by any particular theory, it is believed that the methyl methacrylate crosspolymer serves/acts as an oil absorber, reducing the greasiness of the final product.

Nonetheless, methyl methacrylate crosspolymer is a totally different material than those "oil absorbers" heretofore known to this art, for example the commercially available sport sunscreens indicated above containing hydrophobic silica. Indeed, various diverse materials that are claimed to be "oil absorbers" behave/function quite differently when formulated into sunscreen compositions. As one example, polymethyl methacrylate (Micropearl M100 marketed by Seppic Inc.) was otherwise formulated. It is designated an oil absorber by its supplier, but does not disperse easily into the oil phase of the formulation, resulting in the final composition having an unpleasant, grainy texture.

In the photostable sunscreen formulations according to the present invention, the methyl methacrylate crosspolymer is advantageously present in an amount ranging from about 1% to 10% by weight thereof, more especially from about 1% to 5% w/w thereof.

The subject compositions according to this invention contain an effective UV-photoprotecting amount of at least one UV-A and/or UV-B sunscreen, formulated into a topically applicable, cosmetically/dermatologically acceptable vehicle, diluent or carrier therefor.

By "UV-A and/or UV-B sunscreen" is intended any compound or any combination of compounds which, by mechanisms that are known per se of absorption and/or reflection and/or scattering of UV-A and/or UV-B radiation, prevents, or at least limits, the contact between such radiation and a surface (skin, hair) on which this or these compounds have been applied. Stated differently, these compounds may be UV-absorbing organic screening agents or inorganic (nano) pigments which scatter and/or reflect UV radiation, as well as mixtures thereof.

According to the present invention, the at least one UV-A and/or UV-B sunscreen may comprise one or more hydrophilic organic screening agents and/or one or more lipophilic organic screening agents and/or one or more mineral or inorganic (nano)pigments.

One preferred UV-photoprotecting agent according to the present invention is the dibenzoylmethane sunscreen avobenzone, or 4-(tert-butyl)-4'-methoxydibenzoylmethane, which is very well known to this art, is commercially available and is marketed, for example, under the trademark "PARSOL 1789" by Givaudan. It has the structural formula:

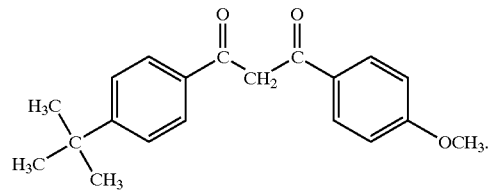

Sunscreens according to the present invention which are physical blockers reflect or scatter ultraviolet radiation. Typical examples of physical blockers include red petrolatum, titanium dioxide, and zinc oxide. These physical blockers have been employed in a variety of suspensions and particle sizes and are frequently included in cosmetic formulations. A review of physical blockers may be found at "Sun Protection Effect of Nonorganic Materials," by S. Nakada & H. Konishi, *Fragrance Journal*, Volume 15, pages 64–70 (1987), which is incorporated by reference herein.

Sunscreens according to this invention which are chemical absorbers, like avobenzone, actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0,933,376, EP-0,893,119, EP-0,669,323, GB-2,303,549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof. Other such representative sunscreens include the dimers derived from (alpha) alkyl styrene compounds, as described in DE 198 55 649, and the 4,4-diarylbutadienes, as described in EP-0,967,200 and DE 197 55 649.

A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Also preferred among those sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis (hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Similarly preferred sunscreens active in the UV-A and/or UV-B range include:

p-aminobenzoic acid, oxyethylene (25 mol) p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammunium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, α-(2-oxoborn-3-ylidene)-tolyl-4-sulfonic acid and soluble salts thereof, 3-(4'-sulfo)benzyliden-bornan-2-one and soluble salts thereof, 3-(4'methylbenzylidene)-d,l-camphor, 3-benzylidene-d,l-camphor, benzene 1,4-di(3-methylidene-10-camphosulfonic) acid and salts thereof (the product Mexoryl SX described in U.S. Pat. No. 4,585,597 issued to Lange et al. on Apr. 29, 1986), urocanic acid, 2,4,6-tris[p-(2'-ethylhexyl-1'-oxycarbonyl)-anilino]-1,3,5-triazine, 2-[(p-(tertiobutylamido)anilino]-4,6-bis-[(p-(2'-ethylhexyl-1'-oxycarbonyl)anilino]-1,3,5-triazine, 2,4-bis{[4-(2-ethyl-hexyloxy)]-2-hydroxy]-phenyl}-6-(4-methoxy-phenyl)-1,3,5-triazine ("TINOSORB S" marketed by Ciba), the polymer of N-(2 et 4)-[(2-oxoborn-3-yliden)methyl] benzyl]-acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and solubilized 2,2'-methylene-bis-[6-(2H-benzotriazol-2-yl)-4-(methyl) phenol] such as that marketed under the trademark MIXXIM BB/200 by Fairmount Chemical.

Typically preferred among the subject sunscreens are one or more of the following: avobenzone, octyl salicylate, octocrylene, and oxybenzone. Combinations of one of more of these sunscreens is similarly preferred.

The dibenzoyl methane derivatives other than avobenzone are also preferred sunscreens according to the present invention. These are described, for example, in FR-2,326,405, FR-2,440,933 and EP-0,114,607, hereby expressly incorporated by reference.

More preferred dibenzoyl methane sunscreens other than avobenzone include (whether singly or in any combination):

2-methyldibenzoylmethane 4-methyldibenzoylmethane 4-isopropyldibenzoylmethane 4-tert.-butyldibenzoylmethane 2,4-dimethyldibenzoylmethane 2,5-dimethyldibenzoylmethane 4,4'-diisopropyldibenzoylmethane 4,4'-dimethoxydibenzoylmethane 2-methyl-5-isopropyl-4'-methoxydibenzoylmethane 2-methyl-5-tert.-butyl-4'-methoxydibenzoylmethane 2,4-dimethyl-4'-methoxydibenzoylmethane 2,6-dimethyl-4-tert.-butyl-4'-methoxydibenzoylmethane The subject at least one UV-A and/or UV-B sunscreen is advantageously formulated into the compositions of the invention in amounts ranging from about 0.01% to about 10%, and preferably from about 0.1% to about 6%, by weight thereof. Of course, depending upon the nature of the particular formulation, higher or lower amounts may be suitable.

Thus, the present invention features topically applicable cosmetic/dermatological compositions, and preferably oil-in-water emulsions/lotions, comprising both at least one UV-A and/or UV-B sunscreen and a methyl methacrylate crosspolymer, formulated into a topically applicable, cosmetically/dermatologically acceptable vehicle, diluent or carrier therefor.

Concordantly, this invention features a regime or regimen for photoprotecting human skin, hair and/or scalp against the damaging or deleterious effects of ultraviolet irradiation, comprising topically applying onto the skin, hair and/or scalp of a human subject, a cosmetic/dermatological composition which comprises (a) an effective UV-photoprotecting amount of at least one UV-A and/or UV-B sunscreen, and (b) an effective dry/nongreasy-imparting amount of methyl methacrylate crosspolymer.

Also featured hereby are concordantly UV-photoprotecting and artificial or sunless tanning compositions comprising those constituents (a) and (b) as indicated above, together with an effective amount of at least one artificial/sunless tanning agent, notably dihydroxyacetone or DHA.

To date, a wide variety of artificial tanning agents has been developed. Artificial tanners provide the highly sought-after tanning or darkening response once only available through harmful exposure to ultraviolet radiation. DHA, in particular, has been widely utilized in cosmetics to accomplish artificial tanning of the skin. Proteins of the epidermis have a very high concentration of arginine, lysine, and histidine and the reaction of skin with DHA to produce an artificial tan takes advantage of this fact. The tanning reaction proceeds through combination with free amino groups in skin proteins, and particularly by combination of DHA with the free guanido group in arginine.

Preferred among those artificial tanners which are useful in the compositions of the instant invention are those selected from the group comprising: allose, alpha hydroxy substituted ketones such as dihydroxyacetone, altrose, arabinose, erythrose, fructose, galactose, glucose, glyceraldehyde, indoles, lactose, mannose, reose, ribose, pentose, sucrose, tallose, xylose, and mixtures thereof.

Most preferred among these artificial/sunless tanners which are useful in the compositions of the present inventions is dihydroxyacetone. In this respect, it should be appreciated that DHA is not at all easy to formulate, is particulary sensitive and compositions comprised thereof tend to be quite unstable over time (as DHA tolerates but few raw materials, e.g., carbomers). Thus, the stable formulations according to the invention, especially those suited for spray delivery or formulated as lotions, are all the more unexpected and surprising.

The compositions of the present invention can be formulated into a wide variety of product types, including creams, dispersions, emulsions (oil-in-water, water-in-oil, water-in-oil-in-water, and oil-in-water-in-silicone), gels, ointments, lotions, milks, mousses, sprays, tonics, and the like. In a most especially preferred embodiment of the present invention, the subject cosmetic/dermatological compositions are provided as lotions.

The topical cosmetic compositions of the present invention typically comprise a carrier (vehicle or diluent) or mixture of carriers. The carrier should be cosmetically and/or pharmaceutically acceptable, which reflects that the carrier is suitable for topical application onto the skin, has good aesthetic properties, is compatible with the copolymer of the present invention, and any other components, and will not cause any untoward safety or toxicity concerns. The carriers and additional components used to formulate such products vary with the product type and may be routinely chosen by one skilled in the art. The following is a description of some of these carriers and additional components.

The compositions of the present invention can comprise a carrier, or a mixture of carriers, suitable for topical application onto human skin. The carriers typically constitute from about 0.5% to about 99.5% by weight, preferably from about 5.0% to about 99.5% by weight, more preferably from about 10.0% to about 98.0% by weight, of the composition. As used herein, the phrase "suitable for topical application onto human skin" reflects that the carrier does not damage or negatively affect the aesthetics of or cause irritation to human skin.

Carriers suitable for use with the present invention include, for example, those used in the formulation of a wide variety of product types, including creams, dispersions, emulsions, gels, lotions, milks, mousses, sprays, and tonics.

The carriers used herein can include a wide range of components conventionally used in cosmetic/dermatological compositions. The carriers can contain a solvent to dissolve or disperse the polymer. The carriers can also contain a wide variety of additional materials including, but not limited to, esters (such as isopropyl myristate), halogenated hydrocarbons (such as freons), hydrocarbons (such as decene, hexane, and isobutane), linalool, volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, dimethicone), alkyl derivatives of benzoic and hydroxybenzoic acid, and mixtures thereof.

Mousses and aerosol sprays can also include any of the conventional propellants to deliver the material as a foam, in the case of a mousse, or as a fine, uniform spray, in the case of an aerosol spray. Examples of suitable propellants include materials such as hydrofluorinated compounds, dichlorodifluoromethane, difluoroethane, dimethylether, isobutane, n-butane, propane, or trichlorofluromethane. A tonic or spray product having a low viscosity may also include an emulsifying agent. Examples of suitable emulsifying agents are anionic surfactants, cationic surfactants, nonionic surfactants, and mixtures thereof. Fluorosurfactants are especially preferred, particularly if the product is a spray composition and most especially if it is a spray composition having a relatively low level of volatile organic solvents, such as alcohols, and relatively high levels of water (i.e., in excess of about 10%, by weight, water). If such an emulsifying agent is included, it is preferably present at a level of from about 0.01% to about 7.5% by weight of the composition. The level of propellant can be adjusted as desired, but is generally from about 3% to about 30% by weight of mousse compositions and from about 15% to about 50% by weight of the aerosol spray compositions.

Suitable spray compositions are well known in the art and include conventional, non-aerosol pump sprays, i.e., "atomizers," aerosol containers or cans having propellant, as described above, and also pump aerosol containers utilizing compressed air as the propellant. Pump aerosol containers are disclosed, for example, in U.S. Pat. No. 4,077,441, issued to Olofsson on Mar. 7, 1978, and U.S. Pat. No. 4,850,517, issued to Ter Stege on Jul. 25, 1989, both incorporated herein by reference.

A wide variety of additional components can be employed in the topical cosmetic/dermatological compositions herein. The compositions of the present invention can comprise a safe and effective amount of a pharmaceutical additive or adjuvant. The phrase "safe and effective" connotes an amount of an active agent high enough to significantly or positively modify the condition to be treated, but low enough to avoid serious side effects (at a reasonable benefit/risk ratio) within the scope of sound medical judgment. A safe and effective amount of the pharmaceutical active agent will vary with the specific active species, the ability of the composition to penetrate the active species through the skin, the amount of composition to be applied, the particular condition being treated, the age and physical condition of the patient being treated, the severity of the condition, the duration of the treatment, the nature of concurrent therapy, and like factors.

Useful pharmaceutical active agents which may be conjointly administered according to the present invention include antimicrobial drugs: antibacterials, antifungals, antiprotozoans, and antivirals. Antimicrobial drugs preferred for inclusion in compositions of the present invention comprise pharmaceutically acceptable salts of β-lactam drugs, amanfadine, amikacin, capreomycin, chlorhexidine, chlortetracycline, ciprofloxacin, clindamycin, doxycycline, erythromycin, ethambutol, gentamicin, kanamycin, lineomycin, methacycline, methenamine, metronidazole, miconazole, minocycline, neomycin, netilmicin, norfloxacin, oxytetracycline, paramomycin, pentamidine, quinolone drugs, streptomycin, tetracycline, tobramycin, and triclosan.

The subject cosmetic/dermatological compositions can contain various emulsifiers when formulated as emulsions. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681, issued to Ciotti et al. on Apr. 30, 1991; U.S. Pat. No. 4,421,769, issued to Dixon et al. on Dec. 20, 1983; and U.S. Pat. No. 3,755,560, issued to Dickert et al. on Aug. 28, 1973. These four publications are incorporated herein by reference in their entirety.

Suitable emulsifier types include acyl lactylates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps and mixtures thereof.

Preferred emulsifiers can include, but are not limited to, ceteareth-20, ceteth-10, cetyl phosphate, diethanolamine cetyl phosphate, glyceryl stearate, PEG-100 stearate, polyethylene glycol 20 sorbitan monolaurate, polyethylene glycol 5 soya sterol, polysorbate 60, polysorbate 80, potassium cetyl phosphate, PPG-2 methyl glucose ether distearate, steareth-20, and mixtures thereof.

Typically preferred among these emulsifiers which are useful in the compositions of the present inventions is PPG-2 isoceteth-20 acetate (described in U.S. Pat. No. 4,559,226, issued to Fogel et al.).

The subject cosmetic/dermatological compositions can also contain various emollients. Examples of suitable emollients include, but are not limited to, highly branched hydrocarbons, non-polar carboxylic acid and alcohol esters, volatile and non-volatile silicone oils, and mixtures thereof. See, U.S. Pat. No. 4,919,934, issued to Deckner et al. on Apr. 24, 1990, which is incorporated by reference in its entirety.

Typically preferred among these emollients which are useful in the compositions of the present inventions are one or more of the following: octyldodecyl neopentanoate and propylene glycol isoceteth-3 acetate.

A variety of additional components can be incorporated into the subject cosmetic/dermatological compositions. Non-limiting examples of these additional components include cationic polymers and thickeners, chelators, gums and thickeners, low pH thickening agents, polymers and materials for enhancing the film-forming and waterproofing properties and substantivity of the composition, sequestrants, skin penetrating aids, suspending agents, vitamins and derivatives thereof, preservatives and aesthetic components.

Exemplary film formers according to this invention (other than the subject MMA crosspolymers) which, upon drying, produce a continuous film on skin, hair, or nails, are described at *CFTA International Cosmetic Ingredient Dictionary and Handbook*, seventh edition, 2, 1636–1638 (1997). These include, for example, varius (meth)acrylate (co)polymers, polyvinyl alcohol, vinyl pyrrolidone (co) polymers, etc.

Exemplary preservatives, which are conventional in this art and which prevent or retard microbial growth and thus protect cosmetic products from spoilage, are set forth at *CFTA International Cosmetic Ingredient Dictionary and Handbook*, seventh edition, 2, 1654 & 1655 (1997).

The cosmetic/dermatological compositions of the present invention are administered in conventional fashion to provide the desired benefit. Such methods of use generally involve topical application of an effective amount of the composition onto the skin, which then is allowed to remain until absorbed into or removed from the skin.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

The following sunscreen plus 3% by weight methyl methacrylate crosspolymer composition was formulated:

| Phase | Ingredient | % |
|---|---|---|
| A | Water | to 100% |
|  | Humectant | 5 |
|  | Panthenol | 1 |
|  | Preservative | 1.25 |
| B | Avobenzone | 3 |
|  | Octocrylene | 10 |
|  | Oxybenzone | 6 |
|  | Octyl Salicylate | 5 |
|  | Emulsifier | 2 |
|  | Emollient | 11 |
|  | PVP/Eicosene copolymer | 1.3 |
|  | Preservative | 0.3 |
|  | Fatty acid/alcohol | 1.5 |
| C | Methyl methacrylate crosspolymer (Canzpearl (3MP-0820) | 3.0 |
| D | Silicone emollient | 3 |

The ingredients of Phase A were introduced into a main tank and heated with homogenization to 80°–85° C. The ingredients of Phase B were combined in a side kettle and heated with moderate propeller mixing to 80° C. Phase C (methyl methacrylate crosspolymer) was slowly added to the side kettle with increased propeller mixing. When the methyl methacrylate crosspolymer was well dispersed, an emulsion was produced by slowly adding the oil phase to the water phase (side kettle to the main kettle) with increased homogenization. The mixing was continued for 15 minutes. Cooling was then initiated and homogenization was decreased. When the contents of the main tank reached a temperature of 50° C., phase D was added to the tank.

EXAMPLE 2

The following sunscreen plus 5% by weight methyl methacrylate crosspolymer composition was formulated:

| Phase | Ingredient | % |
|---|---|---|
| A | Water | to 100% |
| | Humectant | 5 |
| | Panthenol | 1 |
| | Preservative | 1.25 |
| B | Avobenzone | 3 |
| | Octocrylene | 10 |
| | oxybenzone | 6 |
| | Octyl Salicylate | 5 |
| | Emulsifier | 2 |
| | Emollient | 11 |
| | PVP/Eicosene copolymer | 1.3 |
| | Preservative | 0.3 |
| | Fatty acid/alcohol | 1.5 |
| C | Methyl methacrylate crosspolymer (Ganzpearl GMP-0820) | 5.0 |
| D | Silicone emollient | 3 |

The ingredients of Phase A were introduced into a main tank and heated with homogenization to 80°–85° C. The ingredients of Phase B were combined in a side kettle and heated with moderate propeller mixing to 80° C. Phase C (methyl methacrylate crosspolymer) was slowly added to the side kettle with increased propeller mixing. When the methyl methacrylate crosspolymer was well dispersed, an emulsion was produced by slowly adding the oil phase to the water phase (side kettle to the main kettle) with increased homogenization. The mixing was continued for 15 minutes. Cooling was then initiated and homogenization was decreased. When the contents of the main tank reached a temperature of 50° C., phase D was added to the tank.

EXAMPLE 3

The sunscreen formulation of Example 3, containing 5% by weight Ganzpearl GMP-0820, was compared to a similar control formulation not containing the MMA crosspolymer in a sensory study by eleven sensory expert panelists trained in the evaluation and techniques for skin care products.

The purpose of the sensory study was to determine any differences in the application, kinesthetic, visual and tactile attributes between the two sunscreens.

The protocol for the study was as follows:
1. Panelists used a standard cleanser to wash their faces before product application and allowed their skin to equilibrate for 10 minutes.
2. Then 1cc of each product was applied to each side of the face using the 25-rotation method for spreading. The control formulation was applied to the right side of the face and the formulation according to the present invention was applied to the left side of the face.
3. Using the 25-rotation method, panelists determined the type of spread with the first 5 rotations, and whether there was an initial and/or complete absorption.
4. Immediately after spreading the product panelists answered a questionnaire related to the application, kinesthetic, visual and tactile performance of each product.
5. At 3 minutes from the time of application, panelists assessed the waxiness of the respective products.

It was thus determined that significant overall differences existed between the two formulations in terms of product thickness (11.73 vs. 9.91 for visual thickness; 8.77 vs. 8.00 for tactile thickness), absorption (12.55 vs 8.18 for initial absorption; 20.36 vs. 17.45 for complete absorption), drying time (12.14 vs. 13.82), shine (8.18 vs. 4.95), tackiness (2.55 vs. 1.09), waxiness (2.73 vs. 0.91) and greasiness (2.09 vs. 0.91). These numerical comparisons were each on a 15-point scale (0=not at all, with 15=very) and the mean scores for the control formulation are shown first, followed by the mean scores for the formulation according to the invention.

Equally, it was thus found that the formulation according to the invention containing the MMA crosspolymer exhibited considerably less shine, tackiness, greasy feel, and waxy feel than the control formulation. The subject MMA crosspolymer formulation also dried more quickly and was absorbed into the skin more easily on application as compared to the control product.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime/regimen for improvedly UV-photoprotecting human skin, hair and/or scalp against the deleterious effects of ultraviolet irradiation, comprising topically applying thereon a photostable sunscreen formulation which comprises (a) an effective UV-photoprotecting amount of at least one UV-A and/or UV-B sunscreen and (b) an amount of a methyl methacrylate crosspolymer effective to, on application, reduce the greasiness/diffusion and improve the dryness thereof, formulated into (c) a topically applicable, cosmetically/dermatologically acceptable vehicle, diluent or carrier therefor.

2. The UV-photoprotecting regime/regimen as defined by claim 1, said methyl methacrylate crosspolymer comprising particulates of a methyl methacrylate/glycol dimethacrylate crosspolymer.

3. The UV-photoprotecting regime/regimen as defined by claim 2, said crosspolymer particulates having a particle size of less than 20 microns.

4. The UV-photoprotecting regime/regimen as defined by claim 2, said crosspolymer particulates having a particle size of less than 10 microns.

5. The UV-photoprotecting regime/regimen as defined by claim 2, said crosspolymer particulates being essentially spherical in shape and having a particle size ranging from 4 to 8 microns.

6. The UV-photoprotecting regime/regimen as defined by claim 2, said crosspolymer particulates comprising a white fine powder.

7. A regime/regimen for concordantly artificial/sunless tanning and improvedly UV-photoprotecting human skin, hair and/or scalp against the deleterious effects of ultraviolet irradiation, comprising topically applying thereon a photostable sunscreen composition which comprises (a) an effective UV-photoprotecting amount of at least one UV-A and/or UV-B sunscreen, (b) an amount of a methyl methacrylate crosspolymer effective to, on application, reduce the greasiness/diffusion and improve the dryness thereof, and (c) an effective artificial tanning amount of at least one artificial tanning agent, formulated into (d) a topically applicable, cosmetically/dermatologically acceptable vehicle, diluent or carrier therefor.

8. The concordantly artificial/sunless tanning and UV-photoprotecting regime/regimen as defined by claim 7, said at least one artificial tanning agent comprising dihydroxyacetone.

9. A topically applicable cosmetic/dermatological composition suited for improvedly UV-photoprotecting human skin, hair and/or scalp against the deleterious effects of ultraviolet irradiation, comprising (a) an effective UV-photoprotecting amount of at least one UV-A and/or UV-B sunscreen and (b) an amount of a methyl methacrylate crosspolymer effective to, on application, reduce the greasiness/diffusion and improve the dryness thereof, formulated into (c) a topically applicable, cosmetically/dermatologically acceptable vehicle, diluent or carrier therefor.

10. The cosmetic/dermatological UV-photoprotecting composition as defined by claim 9, said methyl methacrylate crosspolymer comprising particulates of a methyl methacrylate/glycol dimethacrylate crosspolymer.

11. The cosmetic/dermatological UV-photoprotecting composition as defined by claim 10, said crosspolymer particulates having a particle size of less than 20 microns.

12. The cosmetic/dermatological UV-photoprotecting composition as defined by claim 10, said crosspolymer particulates having a particle size of less than 10 microns.

13. The cosmetic/dermatological UV-photoprotecting composition as defined by claim 10, said crosspolymer particulates being essentially spherical in shape and having a particle size ranging from 4 to 8 microns.

14. The cosmetic/dermatological UV-photoprotecting composition as defined by claim 10, said crosspolymer particulates comprising a white fine powder.

15. The cosmetic/dermatological UV-photoprotecting composition as defined by claim 10, comprising an oil-in-water emulsion.

16. The cosmetic/dermatological UV-photoprotecting composition as defined by claim 15, comprising a lotion.

17. A topically applicable cosmetic/dermatological composition suited for concordantly artificially/sunless tanning and improvedly UV-photoprotecting human skin, hair and/or scalp against the deleterious effects of ultraviolet irradiation, comprising (a) an effective UV-photoprotecting amount of at least one UV-A and/or UV-B sunscreen, (b) an amount of a methyl methacrylate crosspolymer effective to, on application, reduce the greasiness/diffusion and improve the dryness thereof, and (c) an effective amount of at least one artificial tanning agent, formulated into (d) a topically applicable, cosmetically/dermatologically acceptable vehicle, diluent or carrier therefor.

18. The concordantly artificially/sunless tanning and improvedly UV-photoprotecting cosmetic/dermatological composition as defined by claim 17, said at least one artificial tanning agent comprising dihydroxyacetone.

19. The cosmetic/dermatological UV-photoprotecting composition as defined by claim 10, comprising from 1% to 10% by weight of said methyl methacrylate crosspolymer.

20. The cosmetic/dermatological UV-photoprotecting composition as defined by claim 19, comprising from 1% to 5% by weight of said methyl methacrylate crosspolymer.

* * * * *